United States Patent [19]

Godik

[11] Patent Number: 5,730,133
[45] Date of Patent: Mar. 24, 1998

[54] OPTICAL FUNCTIONAL MAMOSCOPE

[75] Inventor: Eduard E. Godik, Glen Rock, N.J.

[73] Assignee: Dynamics Imaging, Inc., Devon, Pa.

[21] Appl. No.: 664,189

[22] Filed: Jun. 14, 1996

Related U.S. Application Data

[63] Continuation of Ser. No. 246,607, May 20, 1994, abandoned.

[51] Int. Cl.$^6$ .................................................. A61B 5/05
[52] U.S. Cl. ...................... 128/653.1; 128/664; 128/665
[58] Field of Search ........................ 128/653.1, 664, 128/665, 633; 378/37; 250/330

[56] References Cited

U.S. PATENT DOCUMENTS

| | | | |
|---|---|---|---|
| 3,878,392 | 4/1975 | Yew et al. | 250/306 |
| 3,897,150 | 7/1975 | Bridges et al. | 356/5 |
| 4,212,306 | 7/1980 | Mahmud | 128/665 |
| 4,281,645 | 8/1981 | Jöbsis | 128/633 |
| 4,286,602 | 9/1981 | Guy | 128/665 |
| 4,312,357 | 1/1982 | Andersson et al. | 128/664 |

(List continued on next page.)

FOREIGN PATENT DOCUMENTS

| | | | |
|---|---|---|---|
| 0000594 | 8/1979 | European Pat. Off. | 128/664 |
| 0447708 | 9/1991 | European Pat. Off. | 128/664 |
| 0447708A3 | 9/1991 | European Pat. Off. | |
| WO79/00594 | 8/1979 | WIPO. | |

OTHER PUBLICATIONS

Godik, E.E., Guljaev, Yu.V., "The Human Being Through 'Eyes of Radiophysics'", *Journal of Radio Engineering* (Russian) 1991, No. 8, pp. 51–62.

Ring, E.F.J. and Hughes, H. "Real Time Video Thermography", in *Recent Developments in Medical and Physiological Imaging* a supplement to *Journal of Medical Engineering and Technology*, 1986, pp. 86–89.

Platonov, S.A., . . . , Godik, E.E., "Informative Tasks of Functional Mapping of Biological Subjects", *Journal of Radio Engineering* (Russian) 1991, No. 8, pp. 62–68.

Jacquez, J.A. et al, "Spectral Reflectance of Human Skin in the Region 235—1000 nm", *Journal of Applied Physiology*, 1955, vol. 7, No. 3, pp. 523–528.—copy not available.

"Physics of Image Visualization in Medicine", C. Webb, ed. vol. 2, pp. 241–243.—copy not available.

Krenkel, T.E., Kogan, A.G. and Tatatorian, A.M., "Personal Computers in Engineering", Izd. Mir, RiS, (Russian) 1989, pp. 71.—copy not available.

Dgagupov, R.G. and Erofeev, A.A., *Piezo–Ceramic Elements in Instrument Designing and Automatics*, Leningrad, Izd. Mashinosroenie, 1986, pp. 154–155 (Russian).—copy not available.

Svechnikov S.V. "Optoelectronics elements", Moscow, Izd. Sov. Radio 1971, pp. 250–256.—copy not available.

Legett, Kate, *Optical mamography offers promise as alternative to x–ray detection*, Biophotonics International, Jan./Feb., 1996, pp. 56–57. This publication has been submitted as representative of a recent development in the field of mamography.

Godik, Eduard E. and Gulyaev, Uri, V., "Functional Imaging of the Human Body," *IEEE Engineering in Medicine and Biology*, Dec. 1991, pp. 21–29.

*Primary Examiner*—Brian L. Casler
*Attorney, Agent, or Firm*—Jacob N. Erlich; Jerry Cohen

[57] ABSTRACT

The invention belongs to the field of medicine and biology, and more specifically, the invention encompasses an apparatus for performing functional imaging of biological objects. It can be used to distinguish between normal and pathological states in women's mammary glands. The aim of this invention is to increase the reliability of detection of peculiarities in the patient's physiological status, including detection of cancer. Visualization and early diagnosis of different mammary gland pathologies are achieved by recording dynamic images of both mammary glands while illuminating alternatively from opposite sides. The data thus obtained is subsequently combined and processed.

12 Claims, 4 Drawing Sheets

U.S. PATENT DOCUMENTS

| | | | |
|---|---|---|---|
| 4,385,634 | 5/1983 | Bowen | 128/653 |
| 4,495,949 | 1/1985 | Stoller | 128/664 |
| 4,515,165 | 5/1985 | Carroll | 128/664 |
| 4,536,790 | 8/1985 | Kruger et al. | 358/111 |
| 4,570,638 | 2/1986 | Stoddart et al. | 128/665 |
| 4,576,173 | 3/1986 | Parker et al. | 128/633 |
| 4,583,869 | 4/1986 | Chive et al. | 374/122 |
| 4,600,011 | 7/1986 | Watmough | 128/664 |
| 4,649,275 | 3/1987 | Nelson et al. | 250/358.1 |
| 4,767,928 | 8/1988 | Nelson et al. | 250/341 |
| 4,774,961 | 10/1988 | Carr | 128/736 |
| 4,798,209 | 1/1989 | Klingenbeck et al. | 128/653 |
| 4,810,875 | 3/1989 | Wyatt | 128/665 |
| 4,817,038 | 3/1989 | Knoll et al. | 364/413.24 |
| 4,817,622 | 4/1989 | Pennypacker et al. | 128/664 |
| 4,817,623 | 4/1989 | Stoddart et al. | 128/665 |
| 4,829,184 | 5/1989 | Nelson et al. | 128/665 |
| 4,862,894 | 9/1989 | Fujii | 128/666 |
| 4,927,244 | 5/1990 | Bahr et al. | 350/350 S |
| 4,945,239 | 7/1990 | Wist et al. | 250/358.1 |
| 4,948,974 | 8/1990 | Nelson et al. | 250/358.1 |
| 4,955,383 | 9/1990 | Faupel | 128/653 R |
| 4,995,398 | 2/1991 | Turnidge | 128/668 |
| 5,079,698 | 1/1992 | Grenier et al. | 364/413.13 |
| 5,099,848 | 3/1992 | Parker et al. | 128/661.07 |
| 5,139,025 | 8/1992 | Lewis et al. | 128/665 |
| 5,170,119 | 12/1992 | Sekihara et al. | 324/260 |
| 5,197,470 | 3/1993 | Helfer et al. | 128/634 |
| 5,213,105 | 5/1993 | Gratton et al. | 128/664 |
| 5,222,495 | 6/1993 | Clarke et al. | 128/633 |
| 5,269,325 | 12/1993 | Robinson et al. | 128/653.1 |
| 5,293,873 | 3/1994 | Fang | 128/665 |
| 5,301,681 | 4/1994 | DeBan et al. | 128/736 |
| 5,303,026 | 4/1994 | Strobl et al. | 356/318 |
| 5,305,748 | 4/1994 | Wilk | 128/653.1 |
| 5,307,807 | 5/1994 | Valdes Sosa et al. | 128/653.1 |
| 5,309,907 | 5/1994 | Fang et al. | 128/665 |
| 5,311,018 | 5/1994 | Zana et al. | 250/330 |
| 5,313,941 | 5/1994 | Braig et al. | 128/633 |
| 5,333,610 | 8/1994 | Hirao | 128/633 |
| 5,337,745 | 8/1994 | Benaron | 128/633 |
| 5,371,368 | 12/1994 | Alfano et al. | 128/664 |
| 5,515,847 | 5/1996 | Braig et al. | 128/633 |
| 5,555,885 | 9/1996 | Chance | 128/665 |
| 5,572,996 | 11/1996 | Doiron et al. | 128/633 |

OPTICAL FUNCTIONAL MAMOSCOPE

CROSS REFERENCES TO RELATED APPLICATIONS

This application is a continuation of U.S. patent application Ser. No. 08/246,607 filed May 20, 1994 now abandoned.

FIELD OF THE INVENTION

This invention relates to the field of medicine, and more particularly, to apparatus and methods for performing functional mapping of living organisms. Its sphere of application covers a variety of physiological processes taking place in women's mammary glands in their normal state and in the presence of pathology. The aim of the invention is the early visualization and diagnosis of various mammary gland pathologies, including cancer.

BACKGROUND OF THE INVENTION

An apparatus for investigation of the mammary gland is known which employs illumination of the gland and observing the radiation transmitted through the investigated tissues (Mahmud, U.S. Pat. No. 4,212,306). This apparatus is very simple in its realization, but has the considerable disadvantage of not being able to record the spatial distribution of radiation transmitted through the investigated tissue. As a result, unambiguous estimation of the patient's condition is not possible.

An apparatus for performing mammoscopy is taught by Carroll (U.S. Pat. No. 4,515,165) which has the ability to record the spatial distribution of transmitted and back scattered radiation in the visible and infrared ranges. It includes a computer for performing the analysis of static images of the investigated tissue. This apparatus, however, permits the estimation of neither the state of the blood content of the mammary gland's capillary network, nor the functional dynamics of physiological processes related to the state of the entire organism.

An apparatus for the non-invasive investigation of living organism's functional dynamics based on analysis of images of infrared radiation emitted by the investigated organs (thermovision), is known (Godik, E. E. and Guljaev, Yu. V.; Radiotechnics 1991, no. 8 pp. 53–56).

This apparatus consists of a detection system, an interface board and a system for processing and displaying the dynamic images. This apparatus is capable of detecting areas of the investigated organism that are characterized by similar and/or synchronous functional behavior. In other words, it constructs functional maps of physiological processes of the organism. The apparatus has the potential to permit diagnosis of the functional state of capillary microcirculation, for identification of reflective and humoral disturbances of blood vessels as well as revealing precursors of various other pathologies. This apparatus, however, has some considerable disadvantages. Biological tissues are practically opaque for IR-thermal radiation, therefore, any information on the blood content of the tissues located below the thin (100 μm) epidermis cannot be visualized directly. Thermal information from these deeper layers is carried to the surface by means of thermal conductivity rather than direct radiation, resulting in a delay of up to several seconds. As a result, this apparatus is limited to a resolution of several seconds in time and about a millimeter in depth. In addition, this apparatus is not able to investigate changes in blood content distribution past the epidermis.

The closest apparatus to the claimed invention herein is the functional mammoscope (Godik, E. E. and Guljaev, Yu. V.; Radiotechnics 1991, no. 8 pp. 60–61). This instrument is capable of performing multispectral functional mapping of living organisms. Contrary to the above described apparatus based upon thermovision, this instrument is supplied with an illumination source in the 0.6 to 1.3 μm wavelength range, for which biological tissues are known to be quite transparent. The functional mammoscope consists of an illuminator, a mammary gland holder made from transparent plates, and a photo detector system coupled via an interface board to a computer. The interface board performs the analog to digital conversion of the output photodetector signals followed by their input into the computer system as temporal sequences of frames. The computer accumulates the temporal frame sequences, performs spatial and temporal Fourier filtration and differentiates them. In addition, the computer transforms the frame sequences into functional images by detecting areas with similar or synchronous functional behavior over time. These functional images are also called functional maps.

This functional mammoscope apparatus also has considerable disadvantages. First, it does not permit observation and processing of functionally similar areas of both mammary glands simultaneously. According to our data, the correspondence between functional maps generated by both mammary glands simultaneously carries the most valuable information.

Second, illumination of the mammary gland is performed from only one side. Under these conditions, inhomogeneities located near the side opposite the illuminator are most likely to be detected. Inhomogeneities near the side of the gland being illuminated have to be larger and more opaque to be detected due to the scattering of light by the investigated tissues.

Third, this apparatus is not supplied with the necessary facilities for performing necessary functional tests.

SUMMARY OF THE INVENTION

The apparatus of the present inventions overcomes the disadvantages of the apparatus described above. It is characterized by an increased information volume and determines the patients physiological state with high reliability. At the same time it provides sufficiently comfortable conditions for the patient during the investigation procedure.

The apparatus or optical mammoscope of this invention is a modification of the known apparatus and includes an illuminator, a mammary gland holder, and a photodetector connected to a computer via an interface board and includes an additional illuminator supplied with an illuminator control means, an optical means for making adjacent images from images of opposite sides of the mammary gland, an optical commutator and an input-output controller. The optical commutator is placed between the means for making adjacent images and the input to a zoom lens attached to the photodetector means. The optical commutator and the illuminator control means is connected to the computer via the input-output controller.

The present apparatus is also distinguished by inclusion of an additional holder for the second mammary gland along with similar illuminators, optical means and control means as described above.

The present apparatus is further distinguished by the construction of the illuminators as a panel consisting of discrete optical radiation sources coupled to an optical system that projects images of the sources onto the surface of the transparent plates that form the mammary gland holders. These transparent plates are formed from closely packed fiber-optic rods set perpendicular to the surface of the plates, thereby collimating the light passing through the plate.

The illuminators may have a common source of optical radiation and a fiber-optic beam splitter employed to distribute the illumination uniformly over the transparent plates that form the mammary gland holder.

The present apparatus is even further distinguished by the inclusion into the illumination system of at least two sources of optical radiation together with corresponding fiber-optic beam-splitting systems, the output from the latter being distributed evenly inside the transparent plates that form the mammary gland holder.

The present apparatus is further distinguished by the construction of the output elements of the fiber-optic beam splitter mounted in the transparent plates that form the mammary gland holder. The ends of the fibers have rounded ends and are mounted on springs, so that the ends of the fibers protrude from the surface of the plates.

The illumination system of this invention can use either laser diodes, light-emitting diodes, or incandescent lamps as light sources. The system that forms adjacent images from views of opposite sides of the mammary gland is constructed from fiber-optic transmission lines. These adjacent views are imaged onto the photodetectors by a zoom lens. At least one of the transparent plates that form the mammary gland holder is supplied with a moveable diaphragm that can increase or decrease pressure on the gland under control of the computer.

The transparent plates of the mammoscope mammary gland holder are ball-jointed from one side and are supplied with a driver for their controlled movement.

BRIEF DESCRIPTION OF THE DRAWINGS

The claimed apparatus is explained by the drawings, where:

DETAILED DESCRIPTION OF THE PREFERRED EMBODIMENTS

The present invention is based on the formation of dynamic maps of radiation both transmitted and back scattered by the investigated subject. Illumination of both sides of the mammary gland together with an optical system that juxtaposes images of both glands adjacent to one another makes it possible to form dynamic maps of both sides simultaneously by alternately illuminating each side. The time interval between switching the illumination should be chosen to less than that of successive dynamic maps, or between 0.5 and 10 seconds.

Application of the apparatus of this invention (generally in the form of an optical mammoscope) does not have to be restricted to mammary gland imaging, although its advantages are most clearly manifested in mammoscopy. It is possible to investigate other parts of a living organism, provided their dimensions are not too large. This could include the extremities, the head or the body of an infant.

This apparatus permits measurements in several modes: transmitted radiation, back scattered radiation or both transmitted and back scattered radiation.

Whether illumination is provided by projecting light onto the mammary gland, or applying light to the surface of the mammary gland via optical fibers or miniature optical radiation sources, four images of transmitted light are recorded, two from each gland as the light sources alternately illuminate the top or bottom of the gland. Each pair of images characterizes the distribution of inhomogeneities located on the side closest to the detector. Thus, when illumination is applied to the bottom of the gland, functional inhomogeneities located near the upper surface of the gland are seen more clearly, and vice versa.

In the case where both transmitted and back scattered light are recorded, eight images are recorded, four for each gland. The images are recorded nearly simultaneously, thereby providing maximal correlation between the functional maps formed by back scattered radiation from the same side and transmitted radiation from the opposite side. In order to maximize spatial contrast, all four images of one side of both glands are processed simultaneously by the computer system using image correlation methods as described in Platinov, S. A. and Godik, E. E., et al., "Radiotechnics" (Russian) 1991, No. 8, pp. 53–56.

More specifically, the apparatus (or optical mammoscope) contains three main parts: the mammary gland holder that is coupled to the illuminators, a photodetection device with a system for making adjacent images from views of opposite sides of the mammary gland and a computer system for data processing and control of the apparatus.

Figure 1:
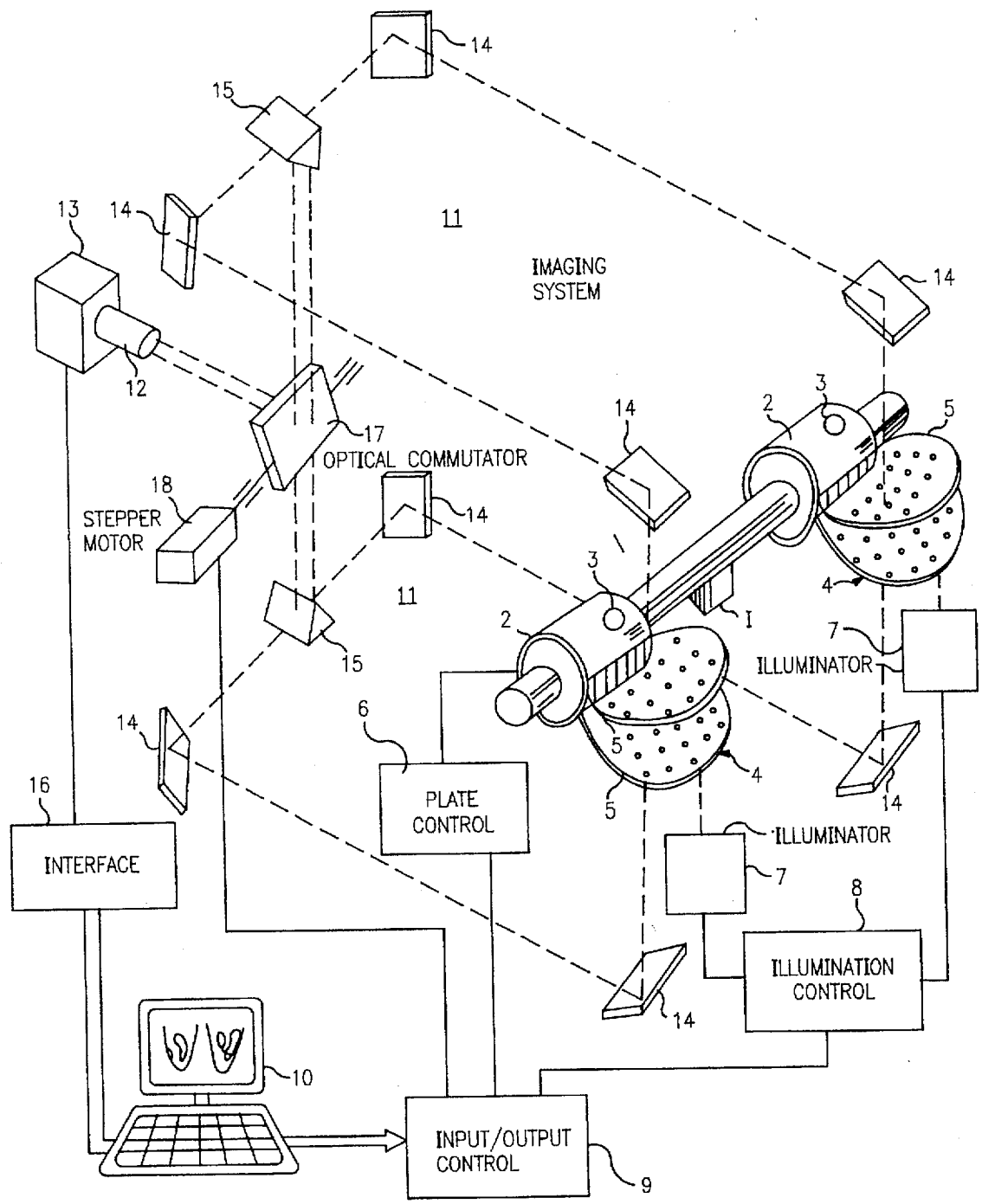
FIG. 1 is a general block diagram of this invention shown partially in schematic fashion.

Reference is now made to FIG. 1 of the drawings which depicts an overall view of the apparatus of this invention showing the stand or support 1 having mechanical translation stages 2 that move horizontally supplied with locking mechanisms 3. The mammary gland holders are formed by optical plates 5 hinged at the translation stages 2. The movement of the optical plates 5 are controlled by the plate control 6. The optical plates 5 are optically coupled to the illuminators 7, which are controlled by the illumination control 8. The computer 10 controls both the plate control 6 and the illumination control 8 via the input-output control 9. An imaging system 11, represented by the dotted lines in FIG. 1, brings together images of both sides of both mammary glands at the input of the zoom lens 12 of the photodetector device 13. The imaging system 11 may be formed by a system of mirrors 14 and 15, aligned in such a way as to juxtapose the images of both of the upper sides and both of the lower sides of the mammary glands. The photodetector device 13 is connected to the computer system 10 via the interface block 16. An optical commutator 17 is placed between optical elements or mirrors 15 of the imaging system 11 to switch between images of both upper or both lower sides of the mammary glands. The optical commutator 17 is actuated by a stepper motor 18 that is controlled by the computer 10 via the input-output control 9. The optical commutator 17 may be a two-sided mirror, in which case the stepper motor 18 can rotate the optical commutator in one direction in 90 degree steps.

In all embodiments of this invention the optical plates 5 are optically coupled with the illuminators 7 irrespective of where the illuminators are placed. Optical radiation from the illuminators 7 can be projected onto the surface of the optical plates via an optical system or connected to them via optical fibers, or the illuminators may be placed directly into the surface of the optical plates.

Figure 2:
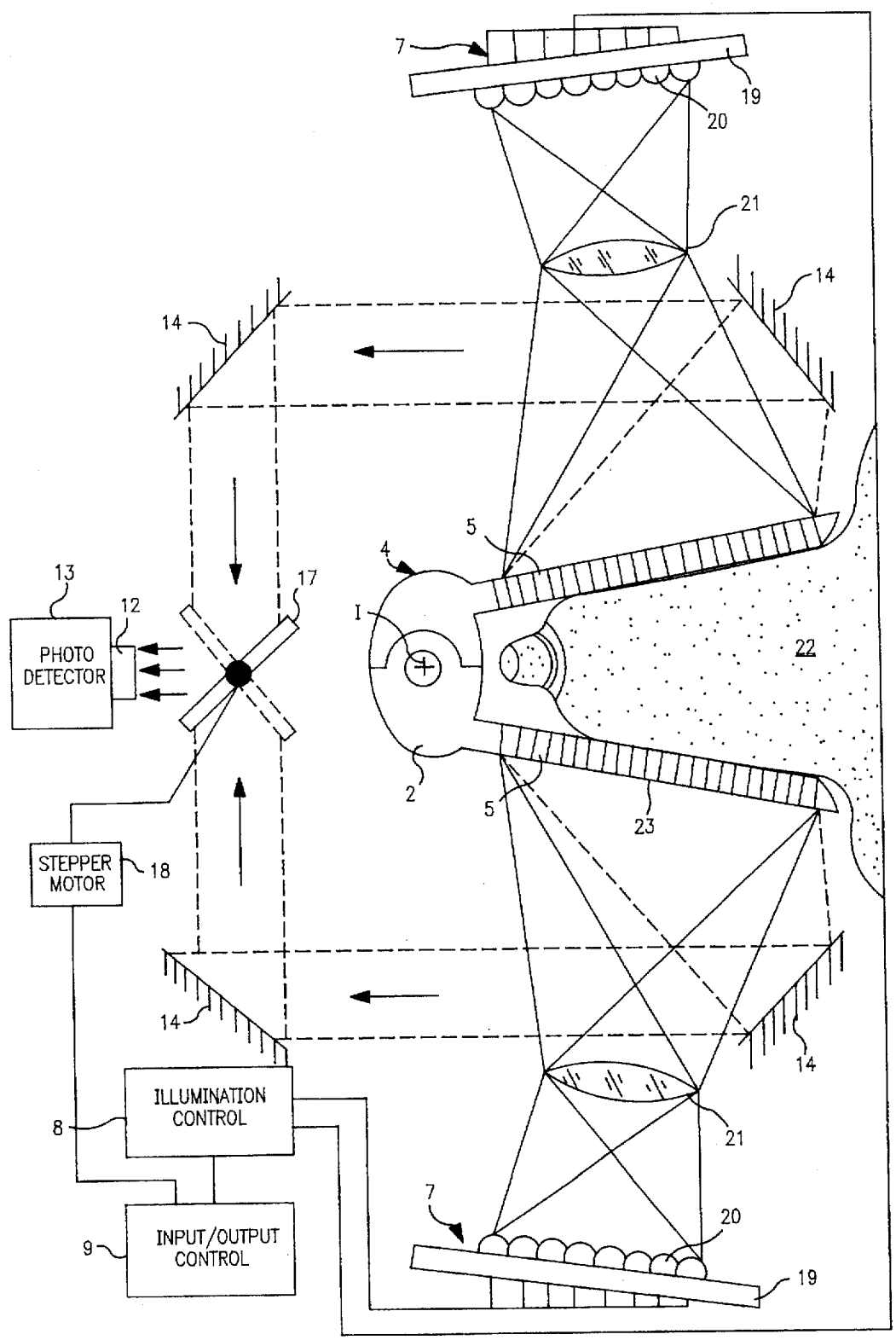
FIG. 2 shows details of the mammary gland holder of this invention in schematic fashion and with block diagrams including the optical system that forms adjacent views of opposite sides of the gland for the case in which projective illumination is used.

FIG. 2 shows another embodiment of this invention that employs projected illumination. Illuminators 7 include a panel 19 in which discrete sources 20 of optical radiation are placed. Each of the sources 20 of optical radiation are connected to the input-output controller 9 via the illuminator control 8, which provides their independent control and regulation.

Figure 3:
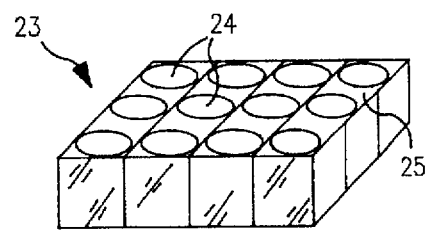
FIG. 3 shows in pictorial fashion a version of the transparent plate design using fiber-optic cylinders to collimate the light passing through the plate.

Still referring to FIG. 2 of the drawings, between the panel 19 and transparent plates 5, a lens system 21 is mounted which projects images of the sources 20 onto the surface of the plates 5. This system is made adjustable to enable the size, form and position of the projected images to be changed. The material that make up the plates 5 is unisotropic, as a result these plates are preferentially transparent to light which strikes the plate perpendicular to its surface and non-transparent to light parallel to the surface, thereby collimating the transmitted light. Collimating the light increases the contrast of the mammary gland images 22. FIG. 3 shows a means for accomplishing this, where optical fibers 24 with a large cross-section and small length are assembled with an ordered disposition in a common glass matrix 25 to form a collimator 23. Such collimators are known elements of optical electronic devices (Svenchikov, S. V., "Optoelectronic Elements," Moscow, Izd. "Soviet Radio" 1971, pp. 250–256). Another possible way to achieve the would be to construct the collimator 23 from an opaque material with through holes perpendicular to the surface of the collimator through which the illumination is transmitted.

For proper alignment of the optical elements, the mammary gland holder 4 may be coupled to the elements of the illumination system 7 and the imaging system 11. Referring to FIG. 2, mirrors 14, lens system 21, and illuminators 19 may all be attached to a common support 1.

The illuminator 7 may be realized as either separate illuminators for each transparent plate 5 or as a single illuminator coupled to the four transparent plates 5 via optical fibers and beam splitters. All elements of the light intensity control, including filters and diaphragms are mounted in each channel of the splitter. The same arrangement of optical fibers and beam splitters is used when separate sources of optical radiation with different wavelengths are employed, with the number of input channels increasing corresponding to the number of additional input sources.

Figure 4:
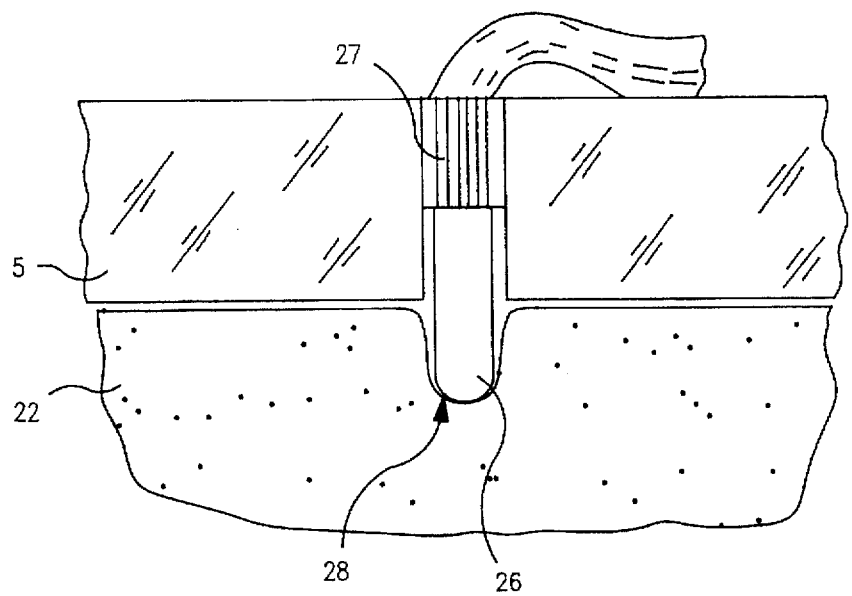
FIG. 4 shows the disposition of the output element of the fiber-optic light beam splitter at the transparent plate showing the rounded end and spring suspension.

FIG. 4 shows the output elements 26 of the beam splitter 27 are placed in the body of the transparent plates 5 uniformly, thereby creating homogeneous illumination over the mammary gland. In addition, the output elements 26 stand out from the plate 5, producing reliable light contact with the mammary gland surface 22. This has the additional effect of excluding any direct illumination of the photodetector device 13. The output elements 26 can additionally be made springy with the addition of spring elements 27. This will not only serve to exclude direct illumination of the photodetector device 13 but also avoid patient discomfort. The working surface 28 of the output elements 26 is rounded and the optical fibers themselves can be terminated either at the outer surface of the transparent plates 5 or in their body.

Figure 5:
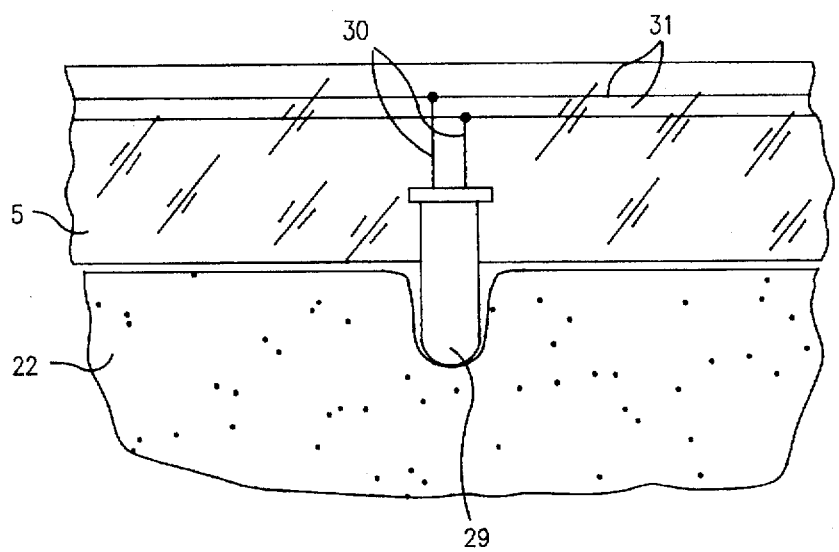
FIG. 5 shows the disposition of the a light emitting diode in the transparent plate.

When miniature sources 29 of optical radiation are used as illuminators, they may be inserted directly into holes made in the transparent plates 5 as shown in FIG. 5. The connection between these sources 29 and the illumination control 8 can be made with the same technology as a printed circuit board, where the traces 30 and 31 can be either formed on the non-working surface of the transparent plates 5 or mounted inside the body. These sources 29 can be incandescent lamps, light emitting diodes or laser diodes. Diodes are preferable since mounting several light emitting or laser diodes that emit different wavelengths permits the selection of the spectral composition of the illumination. FIG. 5 shows an example where a light emitting diode 29 is mounted in a plate 5 and coupled via outputs 30 to the traces 31 that are connected to the illumination control 8. The illumination panel 19 in FIG. 2 may be constructed in a similar fashion.

Figure 6:
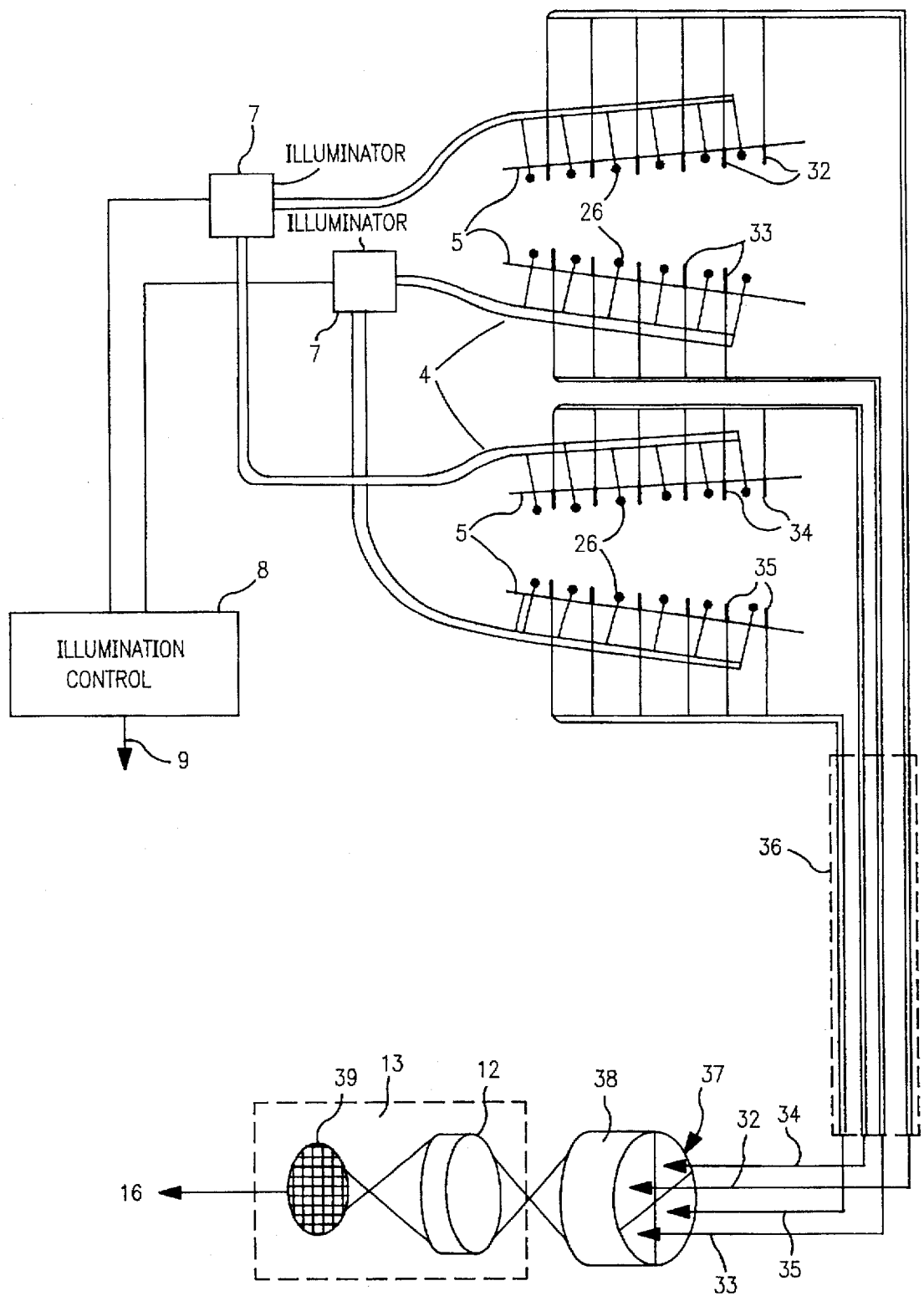
FIG. 6 shows in schematic fashion an alternate embodiment of the present invention using a fiber-optic system of illumination.

FIG. 6 shows another embodiment of the invention using optical fibers for both the imaging and illumination systems. This embodiment uses optical fibers to form adjacent images from images of the opposite side of the mammary glands instead of the mirrors described above.

In FIG. 6 optical radiation from illuminators 7 is transmitted to output elements 26 mounted in the body of the transparent plates 5 as shown in FIG. 4. The output elements 26 are surrounded by the receiving ends of the optical fiber input elements 32, 33, 34, and 35 of image transmission fiber optic 36, having four output optical fibers 37. There is one such image optical fiber 37 for each plate 5. The output fibers 37 are coupled to the zoom lens 12 of the photodetector 13 via the accommodating element 38. The accommodating element 38 can be constructed from gradient refractive index (GRIN) elements. The light sensitive element 39 of the photodetector 13 can be a two-dimensional array of semiconductor photodetectors, for example a charge-coupled device (CCD.)

Input elements 32–35 are distributed over the transparent plates 5 in an ordered manner, but with higher density than the illuminating elements 26 shown in FIG. 4. In addition, they can be supplied with lenses that increase their field of view. These lenses can be constructed as GRIN lenses or other miniature lenses. The input elements are capable of forming images of both the upper and lower parts of the mammary glands and can record both transmitted and back scattered illumination.

A system of fiber-optic image transmission may be realized also for the case where miniature sources 29 of optical radiation are mounted directly in the transparent plates 5.

The illumination control 8 sets the necessary level of illumination intensity and its spectral composition by computer command. This is true for a single source of illumination or for separate sources of illumination. The switching of different light sources or groups of light sources occurs with the help of input-output control 9.

The plate control 6 (FIG. 1), as well as the components that move the transparent plates 5 internally may be realized using known mechanical, hydraulic or pneumatic devices. Their functioning, however, should be "gentle," providing smooth and reliable movement of the plates 5. One function of this mechanism is to provide mammary gland compression, as described by Carr (U.S. Pat. No. 4,774,961, Oct. 4, 1988).

The computer software which processes the acquired data is similar to that described in Godik E. E and Guljaev, Yu. V. "Radiotechnics," (Russian) 1991, No. 8, pp. 53–56 and 60–61 and Platinov, S. A. and Godik, E. E., et al, "Radiotechnics" (Russian) 1991, No. 8, pp. 62–68. The software processes the acquired data and represents it as dynamic maps of the mammary gland's four surfaces simultaneously.

Mode of Operation

The apparatus or optical mammoscope functions in the following manner. First the mechanical translation stages 2 are adjusted with the help of the locking elements 3 to fit the patients mammary glands between the transparent plates 5 of holders 4. The mammary glands are then compressed by the plates 5 under control of the plate control 6.

In all embodiments of the invention, the illuminated areas of the mammary gland 22 are made coincident with the field of view of the imaging system 11, which juxtaposes the images of opposite sides of both glands simultaneously.

The procedure of investigating the mammary glands proceeds as follows. The computer system 10 sends control signals to the illumination control 8, the plate control 6 and the stepper motor 18 via the input-output control 9. The illumination control 8 sets up the necessary spectral composition and intensity of the illumination by controlling the appropriate radiation sources. Stepper motor 18 sets the appropriate position of optical commutator 17. Using these controls, the data can be gathered using the following protocols:

continuous illumination of all four areas.

sequential illumination of the four areas at time intervals much less than the time constant of the investigated process.

pulsed illumination.

Spatial-temporal distributions of the intensity of the transmitted and/or back scattered light recorded by the photodetector device 13 are digitized by the interface block 16 and transmitted to the computer system 10 for processing.

At the spectral ranges where physiological pigments connected with blood and cell metabolisms have their absorption bands, the natural functional dynamics of the living organism's tissues are reflected by the calculated dynamic maps. The appearance of inhomogeneities in the dynamic maps points to the presence of functional disturbances of the tissue investigated, which usually precede the origin of morphological pathology.

When projected illumination is used, as shown in FIG. 2, four dynamic images are obtained, two from each mammary gland. They are formed by transmitted light from illumination of the opposite side of the gland. Each pair of gland images will characterize the distribution of functional inhomogeneities located on the side opposite the illumination.

When both mammary glands are examined, and back scattered light is recorded in addition to transmitted light, eight images are recorded. As was shown above, simultaneously analyzing transmitted and back scattered light increases the spatial contrast of the dynamic maps.

The apparatus of the present invention makes it possible to record the sensitivity of the dynamic images to different functional tests. One possible test is a step-wise reduction in the force compressing the mammary glands. To accomplish this, the transparent plates 5 are released as quickly as possible by means of a step-wise reduction in hydraulic or pneumatic pressure by plate control 6. The dynamic images obtained during the test and immediately after are then analyzed. In order to synchronize the functional test with dynamic image acquisition, plate control 6 can be connected to input-output control 9.

One of the important advantages of this invention is the ability to obtain simultaneous dynamic images of both mammary glands from both the upper and lower sides with alternating illumination. This permits the investigation of spatial inhomogeneities of the functional dynamics whose sources are located deep in the gland.

What is claimed is:

1. An optical mammoscope for simultaneously examining a pair of mammary glands, comprising:

means for positioning said pair of mammary glands for examination, said positioning means including two sets of holders, each movable with respect to the other and each of said holders having a pair of adjustable elements having surfaces for supporting a mammary gland therebetween;

each of said adjustable elements having means operably associated therewith for illuminating the mammary gland with optical radiation and means operably associated therewith for detecting said optical radiation passing through the mammary gland and for providing dynamic images therefrom;

means for simultaneously providing said illumination to one side of both of the mammary glands and for simultaneously providing said illumination, at a predetermined time thereafter, to the other side of both of the mammary glands; and means for analyzing said dynamic images of both of the mammary glands and characterizing a distribution of functional inhomogeneities of the mammary glands located on the sides of the mammary glands opposite said means for illuminating said mammary glands.

2. The optical mammoscope as defined in claim 1 wherein said means for illuminating said mammary gland comprises:

a plurality of panels, each of said panels containing a plurality of discrete sources of illumination and means optically interposed between said sources of illumination and said adjustable element associated therewith, said adjustable elements being made of a material transparent to optical radiation directed perpendicular to its surface and nontransparent to electromagnetic radiation directed parallel to its surface.

3. The optical mammoscope as defined in claim 1 wherein said means for illuminating the mammary gland comprises:

a plurality of optical fibers, each of said optical fibers being operably associated with a different one of said adjustable elements, and each of said adjustable elements having a plurality of output elements optically connected to said optical fiber associated therewith, and a first source of illumination being optically connected to said optical fibers associated with said one side of both of the mammary glands and a second source of illumination being optically connected to said optical fibers associated with said other side of both of the mammary glands.

4. The optical mammoscope as defined in claim 3 wherein said output elements are mounted within said adjustable elements and have rounded portions which extend beyond said surface thereof, pressing against the mammary gland supported by said adjustable elements.

5. The optical mammoscope as defined in claim 1 wherein said means for illuminating the mammary gland comprises:

at least one source of illumination and a series of beam splitters to direct said illumination to said adjustable elements.

6. The optical mammoscope as defined in claim 5 wherein said output elements are spring biased in order to enable the output elements to move relative to said surface of said adjustable element.

7. The optical mammoscope as defined in claim 1 wherein said means for illuminating the mammary gland comprises:

a plurality of individual sources of illumination being located in each of said adjustable elements.

8. The optical mammoscope as defined in claim 1 wherein said detecting means comprises:

a photodetector, means for directing said electromagnetic radiation passing through the mammary gland to said photodetector, and means optically interposed between said photodetector and said directing means for alternating the receipt by said photodetector of said optical radiation based upon which side of the mammary glands said optical radiation has passed through.

9. The optical mammoscope as defined in claim 1 wherein said detecting means comprises:

a plurality of optical fibers, each of said optical fibers having one end thereof optically connected with a different adjustable element, and a photodetecting system optically connected to another end of each of said optical fibers.

10. The optical mammoscope as defined in claim 1 further comprising means for applying pressure to the mammary glands over a predetermined period of time to compress the mammary glands, then in a step-wise fashion reduce the pressure on the mammary glands and perform recording of said dynamic images during and after said stepwise reduction of said pressure.

11. The optical mammoscope as defined in claim 1 further comprising means optically associated with said detecting means for juxtaposing said images of the upper sides of both of the mammary glands and the lower sides of both of the mammary glands.

12. The optical mammoscope as defined in claim 1 wherein said means operably associated with said adjustable elements for detecting said optical radiation passing through the mammary gland also detects backscattered optical radiation from the mammary gland and provides dynamic images therefrom, thereby resulting in eight of said images being acquired for analysis.

\* \* \* \* \*